United States Patent [19]

Mitsuhashi et al.

[11] Patent Number: 4,826,825
[45] Date of Patent: May 2, 1989

[54] DEHYDRATION OF HYDROUS PRODUCT USING ANHYDROUS LACTITOL

[75] Inventors: Masakazu Mitsuhashi; Shuzo Sakai; Toshio Miyake, all of Okayama, Japan

[73] Assignee: Kabushiki Kaisha Hayashibara Seibutsu Kagaku Kenkyujo, Okayama, Japan

[21] Appl. No.: 942,422

[22] Filed: Dec. 16, 1986

[30] Foreign Application Priority Data

Dec. 26, 1985 [JP] Japan .................. 60-292296

[51] Int. Cl.$^4$ .................. A61K 47/00; C08L 5/00
[52] U.S. Cl. .................. 514/53; 514/777; 127/30; 127/38; 426/658; 536/102
[58] Field of Search .................. 514/53, 777; 426/658; 536/102; 127/30, 38

[56] References Cited

U.S. PATENT DOCUMENTS

| | | | |
|---|---|---|---|
| 3,865,957 | 2/1975 | Schieweck et al. | 426/658 |
| 3,957,976 | 5/1976 | Sugimoto | 514/53 |
| 3,973,050 | 8/1976 | Hayashibara et al. | 426/552 |
| 4,102,743 | 7/1978 | Yokobayashi et al. | 435/885 |
| 4,117,173 | 9/1978 | Schiweck et al. | 426/548 |
| 4,146,706 | 3/1979 | Hisatsuka et al. | 536/123 |
| 4,312,979 | 1/1982 | Takemoto et al. | 536/114 |
| 4,359,531 | 11/1982 | Bucke et al. | 426/536 |
| 4,386,158 | 5/1983 | Shimizu et al. | 435/178 |
| 4,556,429 | 12/1985 | Takazoe et al. | 426/658 |
| 4,572,916 | 2/1986 | Lindley et al. | 426/658 |
| 4,659,699 | 4/1987 | Francis | 536/124 |

FOREIGN PATENT DOCUMENTS

| | | |
|---|---|---|
| 0039981 | 5/1981 | European Pat. Off. |
| 448067 | 6/1936 | United Kingdom . |
| 551533 | 2/1943 | United Kingdom . |
| 1247249 | 9/1971 | United Kingdom . |
| 1293477 | 10/1972 | United Kingdom . |

OTHER PUBLICATIONS

*Chemical Abstracts*, vol. 93, No. 19, Nov. 10, 1980, p. 498, col. 2, abstract No. 184334m, Columbus, Ohio, U.S.; P. Linko et al.: "Lactitol" and Carbohydr. Sweeteners Foods Nutr., [Symp] 1978, 243–257.
*Chemical Abstracts*, vol. 91, No. 7, Aug. 13, 1979, p. 32, col. 1, abstract No. 54620z, Columbus, Ohio, U.S.; J. A. Van Velthuijsen "Food additives derived from lactose: Lactitol and lactitol palmitate" and
J. Agric. Food Chem. 1979, 27(4) 680–686.

*Primary Examiner*—Ronald W. Griffin
*Attorney, Agent, or Firm*—Browdy and Neimark

[57] ABSTRACT

A novel dehydration process using anhydrous lactitol as the desiccant is disclosed. Anhydrous lactitol is converted into the crystalline hydrate and acts as the desiccant when incorporated into a hydrous product. The dehydration is applicable to hydrous products, such as foods, pharmaceuticals, cosmetics, and their materials and intermediates.

7 Claims, No Drawings

DEHYDRATION OF HYDROUS PRODUCT USING ANHYDROUS LACTITOL

BACKGROUND OF THE INVENTION

1. Field of the Invention

The present invention relates to a method for dehydration of a hydrous product.

More particularly, the present invention relates to a method for dehydrating a hydrous product characterized by incorporating anhydrous lactitol into the hydrous matter to convert the anhydrous lactitol into crystalline lactitol hydrate.

2. Definition

Throughout the specification, percentages and parts will be expressed by weight based on the dry solid, unless specified otherwise.

3. Description of the Prior Art

The moisture in foods greatly influences the physical properties and shelf lives of foods. Generally, hydrous foods are susceptive to microbial contamination, as well as to alteration and deterioration such as hydrolysis, souring and browning.

As one means to decrease the moisture in the foods in order to prolong their shelf lives, various dehydration methods have been employed: for example, "sato-zuke (preservation in sugar)" as in the case of "buntan-zuke (a candied citrus fruit buntan)", "shio-zuke (pickling in salt)" as in the case of "takuan-zuke (a pickled Japanese radish)", and drying method as in the case of "funmatsu-miso (powdered soybean paste)" or "funmatsu-kaju (fruit juice powder)".

However, sugar has the disadvantages that its excessive sweetness does not suit the recent preference: that the intake of sugar is a major factor of causing dental caries; and still that an excessive intake of sugar increases blood cholesterol. As to common salt, it has been pointed that its excessive intake is one of the major causes of geriatric diseases such as hypertension and cancer. Thus, physicians advise patients to reduce salt intake as much as possible.

Drying undesirably yields insipid foods because vaporization which occurs during drying inevitably disperses some of the compounds responsible for flavor during the processing steps.

Pharmaceuticals containing a bioactive substance, for example, lymphokines, hormones, vitamins, intact bacterial cell or antibiotics, are produced generally by heat-drying or lyophilizing the bioactive substance along with a large amount of a stabilizer. This is because many bioactive substances are unstable under high moisture conditions.

The stabilizers which have been used are water-soluble polymers such as albumin, casein, gelatin and hydroxylethyl starch.

Dehydration in the presence of these water-soluble polymers, however, has the disadvantage of consuming a relatively large amount of energy, insolubilizing the final product, and inactivating the bioactive substances.

SUMMARY OF THE INVENTION

In view of the foregoing, we have investigated the use of lactitol as a desiccant which overcomes these drawbacks of conventional dehydration methods.

As the result, we found that anhydrous lactitol, specifically, a formulation containing a high-purity lactitol with a lactitol content of 90% or higher, act as a strong desiccant when incorporated into hydrous products, such as foods and pharmaceuticals, to effect conversion of the anhydrous lactitol into crystalline lactitol hydrate; as well as that tasty and high-quality dehydrated foods and stable and highly-active pharmaceuticals can be easily prepared in this way.

DESCRIPTION OF THE PREFERRED EMBODIMENTS

The present invention utilizes anhydrous lactitol which has heretofore drawn no attention as a possible desiccant. The present invention is the first instance where a hydrous matter is dehydrated by incorporation of anhydrous lactitol.

The dehydration method according to the invention is advantageous for dehydrating a matter which has a free moisture content but not of a binding water such as water of crystallization, for example, to reduce the moisture in various hydrous products, for example, foods, pharmaceuticals, cosmetics, chemicals, and their materials and intermediates.

We found that incorporation of anhydrous lactitol strongly entraps about 5-10% of moisture from these hydrous products to substantially eliminate their moisture or even to bring them to dryness.

Furthermore, the practice of the present invention leads to no harm because lactitol per se is a non-toxic and harmless natural sweetener. According to the invention, a high-quality food with a substantially-decreased moisture in the form of, for example, massecuite or powder, can be easily prepared by dehydrating a high-moisture content food in liquid or paste form, for example, brandy, fresh cream and mayonnaise. This method has the feature that such a high-moisture content food is easily converted into a tasty dehydrated form without undergoing alteration and deterioration because this method uses no vigorous processing step such as heat-drying.

We found that the inside space of a moistureproof package can be kept at highly-desiccated conditions first by adding anhydrous lactitol in an amount exceeding the moisture in the hydrous food material to be enclosed therein to obtain a dehydrated food wherein the anhydrous lactitol is partially converted into crystalline lactitol hydrate, i.e. a dehydrated food containing both anhydrous lactitol and crystalline lactitol hydrate; then enclosing the dehydrated food in the moistureproof package so as to entrap the moisture in the package with the remaining anhydrous lactitol. This decreases the relative humidity inside the moistureproof package.

Also was found that, as a consequence of the dehydration method, the present invention prevents alteration and deterioration such as microbial contamination, hydrolysis, souring or browning in dehydrated foods; and that the obtained tasty foods retain their quality over a long period of time.

In the case of an aqueous solution of lymphokine or antibiotic, or a paste of pharmaceutical such as ginseng extract or snapping turtle extract, a high-quality pharmaceutical with a substantially-decreased moisture in, for example, massecuite or powder can be easily prepared by incorporating anhydrous lactitol into the aqueous solution or paste to convert the anhydrous lactitol into crystalline lactitol hydrate.

This method provides a high-quality and stable pharmaceutical because the method requires no vigorous processing step such as heat-drying and also because anhydrous lactitol acts as a stabilizer.

Conventional stabilizers such as water-soluble polymer can be suitably used to obtain a much more effectively stabilized pharmaceutical without wasting energy for dehydration of the stabilizer.

The present invention can be advantageously practiced in the preparation of solid injection by, for example, placing a prescribed amount of anhydrous lactitol in a vial; adding to the vial an aqueous solution containing a bioactive substance, for example, lymphokine or hormone, in an amount below the moisture that is required to convert completely the anhydrous lactitol; and sealing the the vial.

We found that, in such case, anhydrous lactitol dehumidifies the air inside the vial, as well as dehydrating the aqueous solution.

Also was found that, as a consequence, the present invention facilitates the preparation of dehydrated pharmaceuticals; and that the obtained pharmaceuticals retain their high quality over a long period of time and readily dissolve in water on use.

The anhydrous lactitol usable in the invention is a substantially-anhydrous lactitol which is convertible into crystalline hydrate to exhibit a strong dehydrating activity. The moisture content of such anhydrous lactitol is generally lower than 3%, preferably, lower than 2%, as measured by the Karl Fischer's method. The anhydrous lactitol may be a commercialized anhydrous crystalline lactitol powder, for example, that available from Hayashibara Biochemical Laboratories Inc., Okayama, Japan, or an anhydrous lactitol powder which is obtainable by heat-drying an aqueous lactitol solution or crystalline lactitol hydrate.

The present invention can be advantageously used when a high-quality dehydrated product in massecuite or powder form is prepared from a hydrous product that is susceptive to alteration and/or deterioration during heat- or vacuum-drying.

The present invention is specifically advantageous when the hydrous products are those of natural origins such as animal, plant or microorganism, such as organ, tissue, cell, triturate, extract component, and preparations obtained therefrom.

In case the hydrous product is a food, its material or intermediate in liquid or paste form, a stable and tasty dehydrated food can be easily prepared according to the invention. Examples of such hydrous product are agricultural products such as fresh fruit, juice, vegetable extract, soybean milk, sesame paste, nut paste, "nama-an (unsweetened bean jam)", gelatinized starch paste and flour dough: marine products such as sea urchin paste, oyster paste and sardine paste; poultry or daily products such as fresh egg, lecithin, milk, whey, fresh cream, yogurt, butter and cheese; hydrous seasonings such as maple syrup, honey, "miso (soybean paste)", soy sauce, mayonnaise, dressing, bonito extract, meat extract, tangle extract, chicken extract, beef extract, yeast extract, mushroom extract, licorice extract, stevia extract, enzymatically processed product thereof and seasoning liquid for pickles; liquors such as Japanese sake, wine, brandy and whisky; soft drinks such as tea, green tea and coffee; hydrous spices such as those extracted from peppermint, "wasabi (Japanese horseradish)", garlic, mustard, "sansho (Japanese pepper tree)", cinnamon, sage, laurel, pepper, and citrus fruits; and hydrous coloring agents such as those extracted from madder, turmeric, paprika, red beet, safflower, cape jasmine, saffron, sorghum and Monascus microorganism.

The dehydrated products obtained in this way, for example, powdered agricultural- or poultry-product, powdered oil and fat, flavor powder and coloring agent powder, can be conveniently used, for example, as a natural bulk flavor excellent in taste and flavor, in various foods, for example, seasonings such as mayonnaise and soup stock; confectioneries such as hard candy and cake; and instant foods such as hot cake mix and instant juice.

In case the hydrous product is a pharmaceutical, its material or intermediate, a stable and highly-active pharmaceutical can be easily prepared without losing or inactivating the effective ingredients. Examples of such hydrous products are a solution containing lymphokine such as interferon, lymphotoxin, tumor necrosis factor, macrophage migration inhibitory factor, colony-stimulating factor, transfer factor or interleukin 2; a solution containing hormone such as insulin, growth hormone, prolactin, erythropoietin or follicle-stimulating hormone; a solution containing a biological such as BCG vaccine, Japanese encephalitis vaccine, tetanus toxoid, Trimeresurus antitoxin or human immunoglobulin; a solution containing antibiotic such as penicillin, erythromycin, chloramphenicol, tetracycline, streptomycin or kanamycin sulfate; a solution containing a vitamin such as thiamine, riboflavin, ascorbic acid, liver oil, carotenoid, ergosterol or tocopherol; a solution containing an enzyme such as lipase, elastase, urokinase, protease, β-amylase, isoamylase, glucanase or lactase; an extract such as ginseng extract, snapping turtle extract, chlorella extract or aloe extract; and cell paste such as that of lactic acid bacterium or yeast.

In case the hydrous product is a cosmetic, its material or intermediate, a high-quality cosmetic can be easily prepared by dehydrating a hydrous product such as fresh egg, lecithin, fresh cream, honey, licorice extract, flavor, coloring agent or enzyme similarly as in the case of foods or pharmaceuticals. The resultant product can be advantageously used as skin- and hair-treatments, and hair tonic.

In case the hydrous matter is an enzyme, the resultant product can be advantagously used in the catalyst for preparing foods, pharmaceuticals and chemicals, as well as in therapeutic, digestive and detergent.

Anhydrous lactitol is incorporated into a hydrous product, for example, by mixing, kneading, dissolving, permeating, sprinkling, coating, spraying or injecting before the processing steps are over.

The amount of anhydrous lactitol to be incorporated is, generally, against one part of a hydrous matter, 0.01–500 parts, desirably, 0.1–100 parts, but varies with the properties of the final product. To improve further the quality of the resultant product, one or more of flavor, coloring agent, seasoning, stabilizer and filler can be used along with anhydrous lactitol.

Such stabilizer may be a water-soluble polymer that has been deemed hardly dehydratable, and is not limited to a low-molecular weight compound such as conventional antioxidant because even such water-soluble polymer is strongly dehydrated with anhydrous lactitol. For this reason, water-soluble polymers, for example, soluble starch, dextrin, cyclodextrin, pullulan, elsinan, dextran, xanthan gum, gum arabic, locust bean gum, guar gum, tragacanth gum, tamarind gum, carboxymethyl cellulose, hydroxyethyl cellulose, hydroxyethyl starch, pectin, agar, gelatin, albumin and casein, can be advantageously used as the stabilizer.

When such water-soluble polymer is used, a dehydrated food with microcrystals of lactitol hydrate can be prepared first by homogenously dissolving a water-soluble polymer in a hydrous product in, for example, liquid or paste form; then incorporating anhydrous lactitol homogenously into the resultant solution with a suitable procedure such as mixing or kneading. In the resultant food, the flavor- and effective-components are coated with a membrane of the water-soluble polymer, or enclosed together with the lactitol hydrate microcrystals in a microcapsule of the membrane. When cyclodextrin is used in combination with anhydrous lactitol, a possible dispersion, alteration and/or deterioration of the above described components is prevented by formation of inclusion complexes. For this reason, this method superiorly retains the flavor- and effective-components that are present in hydrous matters.

In the present invention, various procedures can be used for preparing dehydrated products, specifically, those in pulverulent form. For example, anhydrous lactitol is incorporated homogenously into a hydrous matter, such as food, pharmaceutical, chemical, material or intermediate thereof, with a relatively high moisture to give a moisture content of about 30% or lower, desirably, about 10–25%, and the resultant mixture is allowed to stand at a temperature of about 10°–50° C., for example, ambient temperature, for about 1–10 days to convert the anhydrous lactitol into crystalline lactitol hydrate to obtain a block which is then pulverized by scraping, cutting or crushing. If necessary, drying- and sieving-steps may follow the pulverization.

Spraying method directly provides such powder. For example, a prescribed amount of a hydrous matter in liquid or paste form is sprayed towards a fluidizing anhydrous lactitol to effect granulation, and then aged at about 30°–60° C. for about 1–24 hours to convert the anhydrous lactitol into crystalline lactitol hydrate. Alternatively, a powder obtained by mixing or kneading anhydrous lactitol with a hydrous matter in liquid or paste, and, immediately or after starting the conversion, spraying the resultant mixture is aged similarly. These methods are favorable for preparing a pulverulent product on a large scale.

The spraying method can be advantageously practiced by using a minimum amount of crystalline lactitol hydrate to accelerate the conversion and to shorten the subsequent ageing.

The powder obtained in this way can be shaped, prior to its use, into any form, for example, granule, tablet, capsule, rod, plate or cube, alone or, if necessary, in combination with filler, vehicle, binder and/or stabilizer.

Generally, starch requires a relatively large amount of moisture in its swelling and gelatinization. For this reason, gelatinized starch is susceptive to microbial contamination. Anhydrous lactitol can be advantageously used to dehydrate gelatinized starch. For example, microbial contamination of a gelatinized starch product such as "gyuhi (a rice paste)" can be prevented by incorporating anhydrous lactitol to convert it into crystalline lactitol hydrate and to decrease the moisture in the product.

Furthermore, incorporation of anhydrous lactitol extremely prolongs the shelf lives of processed foods that contain gelatinized starch because anhydrous lactitol disperses homogenously in the gelatinized starch and acts as an agent that prevents retrogradation.

Anhydrous lactitol exhibits a high affinity to alcohols. Because of this property, anhydrous lactitol can be advantageously used as the desiccant for alcohols and alcohol-soluble matters, such as methanol, ethanol, butanol, propylene glycol and polyethylene glycol. For example, a dehydrated liquor in massecuite or powder can be prepared by dehydrating a liquor such as Japanese sake, "shochu (a Japanese distilled spirits,", wine, brandy, whisky or vodka; their effective component and flavor being retained in the resultant crystalline lactitol. The obtained liquor powder can be used in confectioneries and premixes, as well as in beverages after dissolution in water.

In the above case, anhydrous lactitol imparts a mild sweetness, body and appropriate viscosity to the liquor, as well as dehydrating and stabilizing the liquor.

Anhydrous lactitol exhibits an unexpectedly high affinity to oil and fat though it is a hydrophilic saccharide.

Because of this property, anhydrous lactitol can be advantageously used as the desiccant for oil-soluble substances, emulsion or latex, specifically, as the desiccant that entraps the trace moisture in oil-soluble substances. Examples of such oil-soluble substances are fats and oils such as soybean oil, rapeseed oil, mustard oil, sesame oil, safflower oil, palm oil, cacao butter, beef tallow, lard, chicken oil, marine oil and hardened oil; oil-soluble spices such as citrus essential oil, flower essential oil, spice oil, peppermint oil, spearmint oil, cola nut extract and coffee extract; oil-soluble coloring agent such as beta-carotin, paprika pigment, annotto pigment and chlorophyll; oil-soluble vitamins such as liver oil, vitamin A, vitamin $B_2$ lactate, vitamin E, vitamin K and vitamin D; oil-soluble hormones such as estrogen, progesterone and androgen; and unsaturated higher fatty acids such as linoleic acid, linolenic acid, arachidonic acid, eicosapentaenoic acid and docosahexaenoic acid.

The resultant dehydrated oil-soluble substances are characterized by the high-quality and low susceptivity to alteration and deterioration such as hydrolysis and souring.

This method can be advantageously practiced in the preparation of pulverulent foods such as those of oil and fat, spice, flavor and coloring agent, pulverulent cosmetics, and pulverulent pharmaceuticals such as those of vitamin and hormone by impregnating or mixing an oil-soluble substance in anhydrous lactitol.

In this case, anhydrous lactitol acts as the desiccant, as well as a stabilizer, retainer, vehicle and carrier.

As described above, the present invention is based on the finding that anhydrous lactitol strongly dehydrates various hydrous matters. By using anhydrous lactitol as the desiccant, foods, cosmetics and pharmaceuticals that have a decreased moisture and high-quality can be prepared from a hydrous matter in liquid or paste form without causing deterioration and/or dispersion of taste and flavor in foods and cosmetics, and decomposition and/or inactivation of their effective components in pharmaceuticals.

In addition to the above mentioned special uses, anhydrous lactitol can be advantageously used in the preparation of foods, pharmaceuticals and cosmetics because anhydrous lactitol is a natural sweetener and has the inherent feature of lactitol that it imparts a mild sweetness, body, texture, viscosity and moisture-retaining properties to these matters without fear of increasing their cariogenicty and blood cholesterol.

Several embodiments and superior effects of the present invention will be hereinafter described.

EXAMPLE 1

"Oboro-fu gyuhi"

Four kilograms of waxy rice powder was dissolved in 6,000 ml of water, and the resultant mixture was poured into a wet cloth extended over a wooden frame and steamed at 100° C. for 20 minutes. The resultant product was kneaded together with 8 kg of an anhydrous lactitol powder and 1 kg of sucrose, added with 1 kg of corn syrup, sufficiently kneaded, shaped and allowed to stand under ambient conditions for 16 hours to convert the anhydrous lactitol into crystalline lactitol hydrate at the outer layer of the resultant product. Thereafter, the product was subjected briefly to a roll crusher to crack the surface.

The product was excellent in taste and flavor and scarcely susceptive to microbial contamination, and retained its high-quality over a long period of time.

EXAMPLE 2

Fondant containing mayonnaise

Five kilograms of mayonnaise was admixed with 5 kg of an anhydrous lactitol powder to convert it into crystalline lactitol hydrate.

The product can be advantageously used in confectioneries.

The chilled product with a mayonnaise flavor is suitable for frozen dessert.

EXAMPLE 3

French dressing powder

Two kilograms of French dressing was mixed with 8 kg of an anhydrous lactitol powder, transferred into a tray, and blocked by 2-day standing to convert the anhydrous lactitol into crystalline lactitol hydrate.

The block was then pulverized with a scraper and sieved to obtain a French dressing powder excellent in taste and flavor.

The product can be advantageously used for sprinkling on vegetable salad, as well as for seasoning fresh vegetables for sandwich.

EXAMPLE 4

Brandy powder

Ten g of pullulan was dissolved in 2,000 ml of brandy, and the resultant solution was mixed with 10 kg of an anhydrous lactitol powder, blocked and pulverized similarly as in Example 3 to obtained a brandy powder.

The product is a powder flavor that exhibits in the mouth an appropriate sweetness and a satisfactory brandy flavor.

The product can be advantageously used for flavoring tea, as well as preparing confectioneries such as premixes and candies.

The product can be advantageously shaped with granulator or tabletting machine, prior to its use.

EXAMPLE 5

Powdered "miso"

One kilogram of "aka-miso (a reddish soybean paste)" was mixed with 3 kg of an anhydrous lactitol powder, poured into wells provided on a metal plate, solidified by allowing at ambient temperature overnight and removed from the wells to obtain "miso" solids, about 4 g each, which were then subjected to a pulverizer to obtain a "miso" powder.

The product can be advantageously used as the seasoning for instant Chinese noodle and instant "miso" soup.

Additionally, the product is usable in confectioneries.

EXAMPLE 6

Soy sauce powder

One part of "usukuchi-shoyu (a soy sauce with a relatively thin taste)" was sprayed onto 4 parts of an anhydrous lactitol powder powder fluidizing on a conveyer, after which the resultant product was conveyed outside towards an ageing tower and allowed to stand in the tower at 30° C. overnight to convert the anhydrous lactitol into crystalline lactitol hydrate.

The product can be advantageously used as the seasoning for instant Chinese noodle and instant soup.

EXAMPLE 7

Yolk powder

A yolk prepared with fresh eggs was pasteurized at 60°-64° C. with a plate-type heat-pasteurizer, and one part of the obtained yolk fluid was added with 4 parts of an anhydrous lactitol powder, blocked and pulverized similarly as in Example 3 to obtain a yolk powder.

The product can be advantageously used in premixes, frozen desserts and emulsifiers, as well as in baby food and nutritious diet such as liquid food for peroral- or parenteral-administration.

Additionally, the product can be advantageously used in skin treatment and hair tonic.

EXAMPLE 8

Powdered butter

Ten kilograms of butter was mixed with 20 kg of an anhydrous lactitol powder with a mixer, blocked and pulverized similarly as in Example 3 to obtain a butter powder.

The product can be advantageously used in premix, potage soup, stew and "chahan (a Chinese fried rice)", as well as in nutritious diet such as intubation feeding.

EXAMPLE 9

Cream powder

Two kilograms of fresh cream was mixed with 8 kg of an anhydrous lactitol powder, blocked and pulverized similarly as in Example 3 to obtain a cream powder.

The cream powder excellent in taste and flavor can be advantageously used for seasoning coffee and tea, as well as preparing premix, frozen dessert, cake, candy and nutritious diet such as intubation feeding.

Also, the product can be advantageously used in skin treatment and hair tonic.

EXAMPLE 10

Yogurt powder

Two kg of plain yogurt was mixed with 10 kg of an anhydrous lactitol powder, blocked and pulverized similarly as in Example 3 to obtain a yogurt powder.

The product is excellent in taste and flavor, and stably retains the lactic acid bacteria over a long period of time. The product can be advantageously used to prepare premix, frozen dessert and cake, as well as to prepare nutritious diet such as intubation feeding.

The biochemicals obtained by shaping the product with a granulator or tabletting machine can be advantageously used as the medicine for intestinal disorders.

EXAMPLE 11

Hot cake mix

Two hundred grams of flour was mixed with 60 g of a yolk powder obtained by the method in Example 7, 78 g of a butter powder obtained by the method in Example 8, 10 g of sucrose, 12 g of baking powder and 0.5 g of salt to obtain a hot cake mix.

A tasty hot cake can be easily prepared by dissolving the product in water or milk, and baking the resultant mixture.

EXAMPLE 12

Ginseng extract powder

Five hundred grams of ginseng extract was kneaded with 1.5 kg of an anhydrous lactitol powder, blocked and pulverized similarly as in Example 3.

The resultant powder was then fed to a granulator together with appropriate amounts of vitamin $B_1$ and vitamin $B_2$ powders to obtain a ginseng granule containing vitamins.

The product can be advantageously used as tonic, hair treatment and medicine for relieving fatigue.

EXAMPLE 13

Solid composition for fluid food

Twenty-five gram aliquots of a composition consisting of 500 part of an anhydrous lactitol powder, 270 parts of a yolk powder obtained by the method in Example 7, 209 parts of defatted milk, 4.4 parts of sodium chloride, 1.85 parts of potassium chloride, 4 parts of magnesium sulfate, 0.01 part of thiamine, 0.1 part of sodium ascorbate, 0.6 parts of vitamin E acetate, and 0.04 parts of nicotinamide were packed in small moistureproof laminated bags, followed by heat-sealing.

The composition decreases the moisture in the bag and requires no low-temperature storage because it is stable over a long period of time even at ambient temperature.

The product is excellently dispersible and soluble in water.

One pack of the product, dissolved in about 150–300 ml of water, can be used as the liquid food in peroral- or parenteral-administration through the nasal cavity, stomach or intestine.

EXAMPLE 14

Solid injection

Newborn hamsters were injected with antiserum prepared in conventional manner to weaken their immunoreaction, implanted subcutaneously with BALL-1 cells and fed in the usual manner for 3 weeks. The tumor masses, formed subcutaneously in the body of the hamsters, were extracted, minced and disaggregated in saline. The cell mass thus obtained was washed with serum-free RPMI 1640 medium (pH 7.2), suspended in a fresh preparation of the same culture medium to give a cell density of about $2 \times 10^6$ cells/ml, and incubated at 35° C. The culture medium was added with 200 U/ml of a partially-purified human interferon, incubated at this temperature for an additional 2 hours, added with about 300 hemagglutination titer/ml of Sendai virus, and incubated for an additional 20 hours to induce human interferon production. The resultant culture was then centrifuged at about $1,000 \times g$ and 4° C. to remove the sediment, and the supernatant was filtered with a membrane filter. The filtrate was passed through a column of immobilized anti-interferon antibody in conventional manner, and the non-adsorbed part was removed. The adsorbed part was then eluted and concentrated with a membrane to obtain a liquid preparation, concentration of about 0.01 w/v %, specific activity of about $1.5 \times 10^8$ U/mg protein, in the yield of about 4 ml per hamster.

Eight gram aliquots of a pyrogen-free anhydrous lactitol were placed in 100 ml moistureproof plastic bottles which were then added with 0.2 ml aliquot of the interferon concentrate (about $3 \times 10^6$ U), rubber-stopped and cap-sealed sterilely to obtain a solid injection.

This process has the advantages that it requires no treatment, apparatus and energy for lyophilization because the interferon-containing solution is dehydrated only by adding dropwisely it to a portion of anhydrous lactitol powder, as well as that it effectively stabilizes interferon.

Since the product is readily dissolvable in water, it can be advantageously used as the test reagent, antiviral agent or antioncotic for subcutaneous, intramascular or intravenous injection.

The titer of human interferon was assayed by the conventional plaque reduction method, and the hemagglutination titer was measured by the method as reported by J. E. Salk, *The Journal of Immunology*, Vol. 49, pp. 87–98 (1944).

EXAMPLE 15

Solid injection

Newborn hamsters were injected with an antiserum prepared from rabbit in conventional manner to weaken their immunoreaction, implanted subcutaneously with an established SV-40 virus-transformed human monocyte, fed in usual manner for one week, injected intraperitoneally with $10^7$ viable BCG cells and fed for an additional 2 weeks. The tumor masses, formed subcutaneously in the body of the hamsters, about 15 g each, were extracted, minced and disaggregated by suspending in saline containing trypsin. The obtained cell was washed with Eagle's minimal essential medium (pH 7.2), supplemented with 5 v/v % human serum, diluted with a fresh preparation of the same culture medium, prewarmed to 37° C., to give a cell density of about $5 \times 10^6$ cells/ml, added with about 10 μg/ml of *E. coli* endotoxin, and incubated at this temperature for 16 hours to induce tumor necrosis factor production.

The resultant culture was then centrifuged at about $1,000 \times g$ and 4° C. to remove the sediment, and the supernatant was dialyzed against saline containing 0.01 M phosphate buffer (pH 7.2) for 21 hours, filtered with a membrane filter, concentrated and lyophilized to obtain a powder possessing tumor necrosis factor activity. The obtained powder was then purified with adsorption and desorption using ion exchange, molecular weight fractionation using gel filtration, concentration and filtration using membrane filter in accordance with the method as reported in G. Bodo, *Symposium on Preparation, Standardization and Clinical Use of Interferon*, 11th International Immunobiological Symposium 8 & 9, June 1977, Zagreb, Yugoslavia, to remove the interferon, and the resultant interferon-free product was purified by salting-out using ammonium sulfate and affinity-chromatography using concanavalin A-bound Sepharose to obtain an about 0.01 w/v % concentrate containing tumor necrosis factor in the yield of about 30 ml per hamster. Tumor necrosis factor is characterized in that it effects hemorrhagic cytolysis on Meth A sarcoma but no affects on normal human cells. The tumor necrosis factor obtained in this way was a glycoprotein with a specific activity of about $3.5 \times 10^5$ U/mg protein and free of the inducer used.

Fifty gram aliquots of a pyrogen-free anhydrous lactitol were placed in 600 ml glass bottles, added with 0.5 ml of the concentrate containing tumor necrosis factor (about $1.75 \times 10^3$ U), rubber-stopped and cap-sealed under sterilely to obtain a solid injection.

This process has the advantages that it requires no treatment, equipment and energy for lyophilization because the solution containing tumor necrosis factor is dehydrated by anhydrous lactitol powder, as well as that it effectively stabilizes tumor necrosis factor.

Since the product is readily dissolvable in water, it can be advantageously used as the antioncotic, hyperalimentation and injection for instillation.

The titer of tumor necrosis factor was assayed by the method in *Lymphokines*, Vol. 2, pp. 235-272 "Tumor Necrosis Factor" (1981), wherein L-929 cell that is sensitive to tumor necrosis factor is cultured for a prescribed time, followed by counting of the number of the viable cells.

As is apparent from the above, the present invention relates to a dehydration method wherein a hydrous product is dehydrated by incorporating into it an anhydrous lactitol to convert it into crystalline lactitol hydrate. The present invention can be advantageously used to decrease the moisture content of various hydrous matters, for example, foods, pharmaceuticals, cosmetics, chemicals, and their materials and intermediates.

Since, in the present invention, a substantial dehydration is effected by converting an anhydrous lactitol into crystalline lactitol hydrate, therefore, vigorous processing conditions conditions such as heat-drying are not required, and high-quality dehydrated products can be prepared without deteriorating hydrous products, for example, foods which tend to lose their flavor, and pharmaceuticals which tend to decompose or inactivate their effective ingredient.

The dehydrated products obtained in this way retain their high-quality over a long period of time because alteration and deterioration such as microbial contamination, hydrolysis, souring and browning are prevented in the product.

While a preferred embodiment of the invention has been described using specific terms, such description is for illustrative purpose only, and it is to be understood that changes and variations may be made without departing from the spirit or scope of the following claims.

We claim:

1. A method for dehydrating a hydrous product, comprising incorporating anhydrous lactitol into an hydrous product to convert said anhydrous lactitol into crystalline lactitol hydrate.

2. The method of claim 1, wherein said anhydrous lactitol is a high-purity lactitol having a lactitol content of 90% or higher, based on the dry solid.

3. The method of claim 1, wherein said anhydrous lactitol is in pulverulent form.

4. The method of claim 1, wherein the moisture content of said anhydrous lactitol is lower than 3 w/w %.

5. The method of claim 1, wherein 0.01 to 500 parts by weight of anhydrous lactitol is incorporated into one part by weight of a hydrous product.

6. The method of claim 1, wherein said hydrous product is a member selected from the group consisting of food products, pharmaceuticals, cosmetics, and material and intermediates thereof.

7. The method of claim 1, wherein said hydrous product contains a member selected from the group consisting of gelatinized starches, alcohols, oil-soluble substances and bioactive substances.

* * * * *